US00PP35307P2

(12) United States Plant Patent
Moon

(10) Patent No.: US PP35,307 P2
(45) Date of Patent: Aug. 8, 2023

(54) ***LIRIODENDRON* TREE NAMED 'LTMTF'**

(50) Latin Name: *Liriodendron tulipifera*
Varietal Denomination: LTMTF

(71) Applicant: Dwayne Moon, Washington, GA (US)

(72) Inventor: Dwayne Moon, Washington, GA (US)

( * ) Notice: Subject to any disclaimer, the term of this patent is extended or adjusted under 35 U.S.C. 154(b) by 0 days.

(21) Appl. No.: 17/903,670

(22) Filed: Sep. 6, 2022

(51) Int. Cl.
*A01H 5/00* (2018.01)
*A01H 6/00* (2018.01)

(52) U.S. Cl.
USPC ..... Plt./216

(58) Field of Classification Search
USPC ..... Plt./216
See application file for complete search history.

*Primary Examiner* — Susan McCormick Ewoldt
(74) *Attorney, Agent, or Firm* — Cassandra Bright

(57) ABSTRACT

A new and distinct cultivar of *Liriodendron tulipifera* tree named 'LTMTF' is disclosed, characterized by a upright form with a central leader and dense canopy. Dark green foliage color is maintained to late Fall. A fast growth rate has been observed, as has easy rooting. The new variety is a *Liriodendron* tree, typically used for landscapes and gardens.

3 Drawing Sheets

Latin name of the genus and species: *Liriodendron tulipifera.*

Variety denomination: 'LTMTF'.

BACKGROUND OF THE INVENTION

The new cultivar is a product of a planned breeding program. The new variety was discovered growing as a seedling among a group of crossbred *Liriodendron tulipifera* trees of the general species at a tree farm in Washington, Ga. The inventor made this discovery in the fall of 2014. The exact seed and pollen parents cannot be identified.

Asexual reproduction by grafting of the new cultivar 'LTMTF' was first performed during winter of 2015 at a farm in Washington, Ga. The cleft grafting system developed by the inventor has resulted in progeny that have proven the characteristics of the new variety to be genetically stable. This grafting process involved taking cuttings in February, being grafted, and being placed in calloused chambers for approximately three weeks. They are then moved into 3"×6" tree band pots and placed in humidity chambers for approximately four weeks. Furthermore, these observations have confirmed that the new variety represents a new and improved variety of *Liriodendron tulipifera* tree as particularly evidenced by the fastigiate growth habit. These genetic traits can be consistently reproduced by asexual propagation.

SUMMARY OF THE INVENTION

The cultivar 'LTMTF' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'LTMTF' grown in Washington, Ga. These characteristics in combination distinguish 'LTMTF' as a new and distinct *Liriodendron tulipifera* cultivar:

1. Upright form with central leader.
2. Dark green foliage which resists insects and disease.
3. Dense throughout canopy.
4. Fast growth.
5. Attractive foliage dark green foliage to late Fall.
6. Easy to root.

PARENT COMPARISON

Parent varieties have not been identified.

COMMERCIAL COMPARISON

Plants of the new cultivar 'LTMTF' are similar to plants of *Liriodendron tulipifera* 'Ardis', unpatented, in most horticultural characteristics, however, plants of the new cultivar 'LTMTF' differ in the following:

1. The new variety is taller than this comparator.
2. The new variety has a larger leaf than this comparator.

Plants of the new cultivar 'LTMTF' are similar to plants of *Liriodendron tulipifera* 'Aureomarginatum', unpatented, in most horticultural characteristics, however, plants of the new cultivar 'LTMTF' differ in the following:

1. The new variety has solid colored foliage; this comparator has variegated foliage.
2. The new variety has a narrow habit.

Plants of the new cultivar 'LTMTF' are similar to plants of *Liriodendron tulipifera* 'Compactum', unpatented, in most horticultural characteristics, however, plants of the new cultivar 'LTMTF' differ in the following:

1. This comparator is about half size of the new variety.

Plants of the new cultivar 'LTMTF' are similar to plants of *Liriodendron tulipifera* 'JFS-Oz', unpatented, in most horticultural characteristics, however, plants of the new cultivar 'LTMTF' differ in the following:

1. The new variety has a narrower canopy than this comparator.

Plants of the new cultivar 'LTMTF' are similar to plants of *Liriodendron tulipifera* 'Fastigiatum', unpatented, in most horticultural characteristics, however, plants of the new cultivar 'LTMTF' differ in the following:

1. The new variety has a broader canopy than this comparator.

Plants of the new cultivar 'LTMTF' are similar to plants of *Liriodendron tulipifera* 'Glen Gold', unpatented, in most horticultural characteristics, however, plants of the new cultivar 'LTMTF' differ in the following:

1. The new variety does not have the yellow young foliage color found in this comparator.

Plants of the new cultivar 'LTMTF' are similar to plants of *Liriodendron tulipifera* 'Integrifolium', unpatented, in most horticultural characteristics, however, plants of the new cultivar 'LTMTF' differ in the following:

1. Leaf shape of the new variety is broad orbicular with 4 lobes; in this comparator lower lobes are missing resulting in almost rectangular leaf.

Plants of the new cultivar 'LTMTF' are similar to plants of *Liriodendron tulipifera* 'Little Volunteer', U.S. Plant Pat. No. 19,581, in most horticultural characteristics, however, plants of the new cultivar 'LTMTF' differ in the following:

1. This comparator has a very dwarf habit, about one-third the size of the new variety.

Plants of the new cultivar 'LTMTF' are similar to plants of *Liriodendron tulipifera* 'Mediopictum', unpatented, in most horticultural characteristics, however, plants of the new cultivar 'LTMTF' differ in the following:

1. Foliage of the new variety are solid green; leaves of this comparator are green with a yellow blotch in the middle.
2. Bright green leaves.

Plants of the new cultivar 'LTMTF' are similar to plants of *Liriodendron tulipifera* 'Purgatory', unpatented, in most horticultural characteristics, however, plants of the new cultivar 'LTMTF' differ in the following:

1. Foliage of the new variety are solid green; leaves of this comparator are mottled yellow and green variegated leaves.

Plants of the new cultivar 'LTMTF' are similar to plants of *Liriodendron tulipifera* 'Ramapoo', unpatented, in most horticultural characteristics, however, plants of the new cultivar 'LTMTF' differ in the following:

1. Leaf shape of the new variety is broad orbicular with 4 lobes; leaves of this comparator are almost lobeless with rounded leaves.

Plants of the new cultivar 'LTMTF' are similar to plants of *Liriodendron tulipifera* 'Roodhan', unpatented, in most horticultural characteristics, however, plants of the new cultivar 'LTMTF' differ in the following:

1. Foliage of this comparator is lighter green with more lobes than the new variety.

Plants of the new cultivar 'LTMTF' are similar to plants of *Liriodendron tulipifera* 'Tennessee Gold', unpatented, in most horticultural characteristics, however, plants of the new cultivar 'LTMTF' differ in the following:

1. Foliage of the new variety are solid dark green; leaves of this comparator are yellow-green.

Plants of the new cultivar 'LTMTF' are similar to plants of *Liriodendron tulipifera* 'Tortuosum', unpatented, in most horticultural characteristics, however, plants of the new cultivar 'LTMTF' differ in the following:

1. This comparator has contorted stems not found in the new variety.

BRIEF DESCRIPTION OF THE PHOTOGRAPHS

The accompanying photograph in FIG. 1 illustrates multiple trees of the new variety at about 3 years of age.

Figure 1:
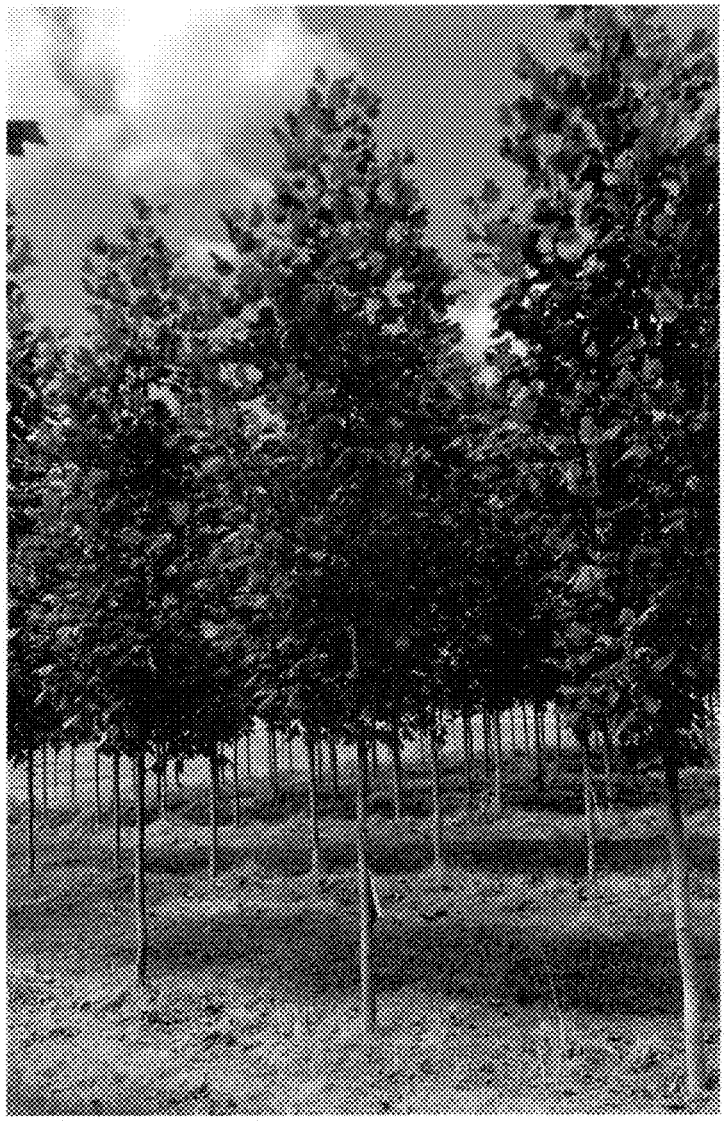
Figure 2:
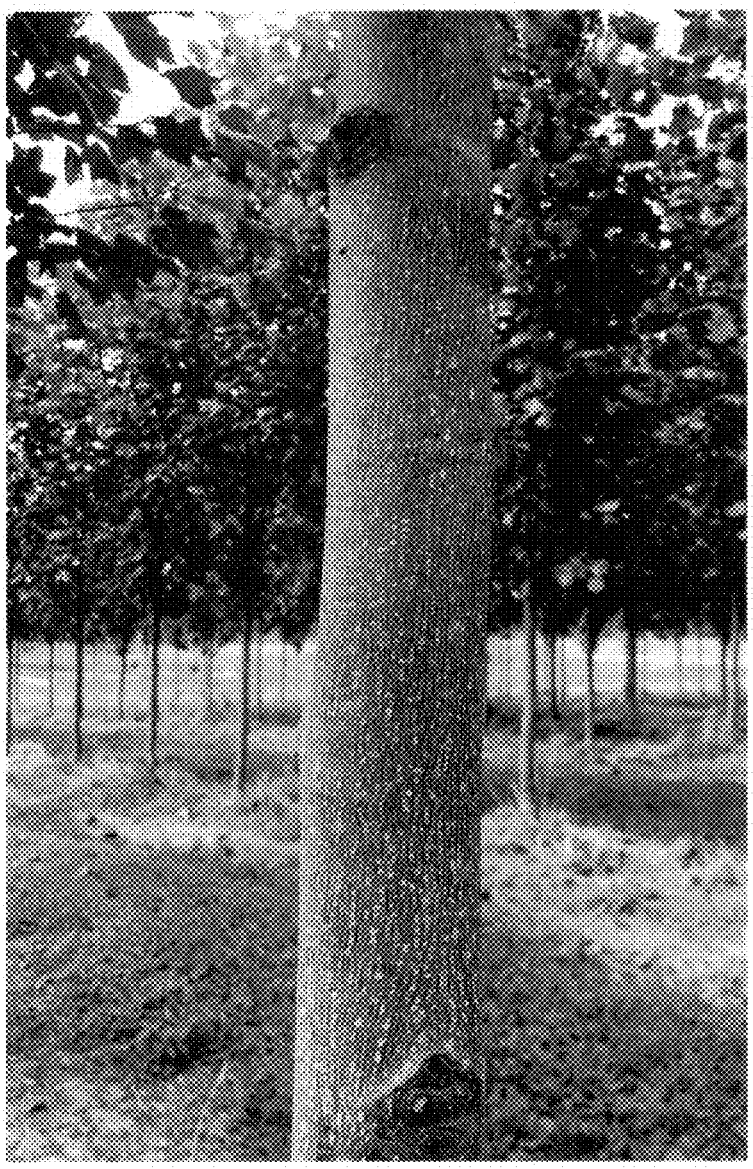
FIG. 2 illustrates a close-up view of the trunk.
Figure 3:
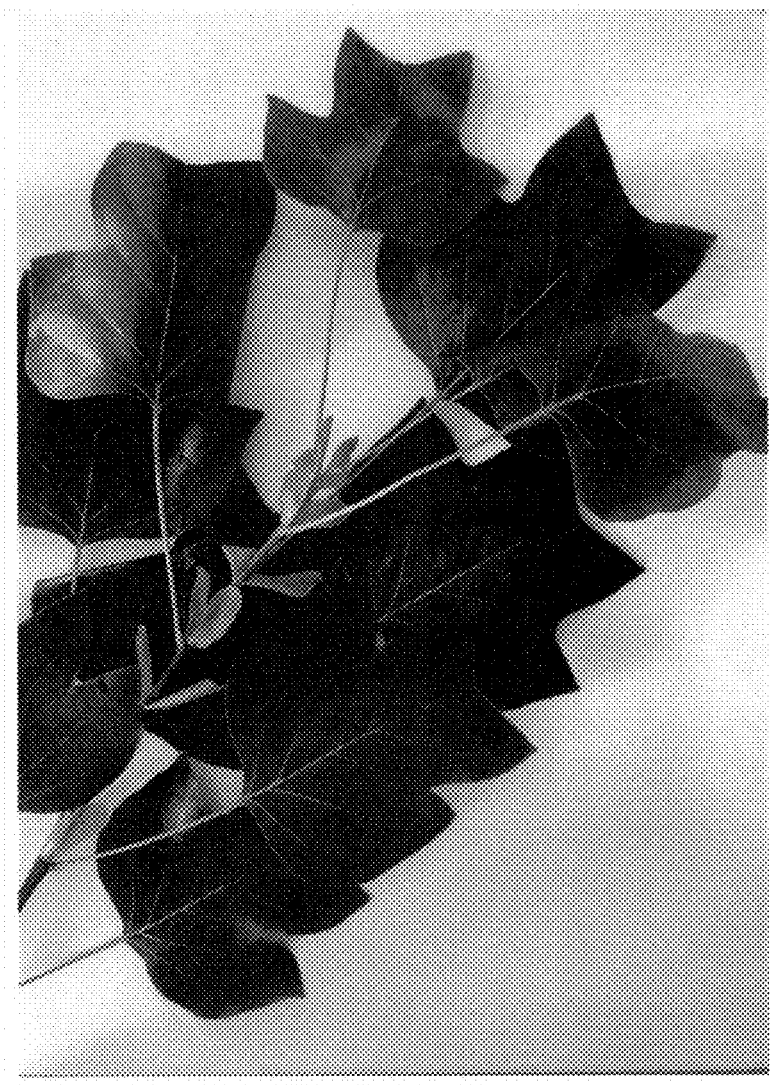
FIG. 3 illustrates foliage of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'LTMTF' plants grown outdoors and in a nursery in Washington, Ga. Plants are approximately 2 years old, in a 3 gallon nursery container. Temperatures ranged from 2° C. to 10° C. at night to 18° C. to 39° C. during the day. Measurements and numerical values represent averages of typical plant types.

Botanical classification: *Liriodendron tulipifera* 'LTMTF'.

PROPAGATION

Cleft grafting.

TREE

Growth habit: Deciduous tree with a dense canopy in a narrow oval shape. Central leader.

Height: Approximately 20 feet at 3 years.

Spread: Approximately 7 feet at 3 years.

Growth rate: Rapid.

Branch characteristics:

- *Length*.—Average Range 50 to 75 cm.
- *Diameter*.—Average 2 cm.
- *Color*.—Near RHS Greyed-Green 194A flushed Greyed-Purple 183C.
- *Texture*.—Smooth.
- *Angle*.—Acute, 35° or less.
- *Aspect*.—Straight.

Trunk characteristics:

- *Diameter*.—About 3.5 inches measured at approximately 3 inches above soil level at 3 years.
- *Color*.—Near RHS Grey 201C with square blotches near Greyed-Green 198D.
- *Surface texture*.—Narrow, irregular furrows.

FOLIAGE

Leaf:

- *Arrangement*.—Alternate.
- *Shape*.—Overall broad orbicular; 4 lobes of bilateral symmetry. Lateral sinus about 3 cm deep, apical sinus about 1.5 cm deep. Length between lateral lobe apex to apical lobe apex about 3 cm.
- *Average length*.—Approximately 10 cm excluding petiole.
- *Average width*.—Approximately 13 cm.

*Apex*.—Broad angular lobe with two acute lobe aspices.
*Base*.—Obtuse.
*Margin*.—Entire.
*Texture of top surface*.—Glabrous.
*Texture of lower surface*.—Glabrous.
*Color*.—Young foliage: Upper side: Near RHS Green 137A. Under side: Near RHS Green 138B. Mature foliage: Upper side: Near RHS Green 139A. Under side: Near RHS Green 138A.
*Venation*.—Type: Pinnate. Color: Venation color upper side: Near RHS Yellow-Green 144B. Venation color under side: Near RHS Yellow-Green N144A.
*Petiole*.—Length: Average 8 cm. Diameter: Average 2 to 4 mm. Color: Upper side: Near RHS Yellow-Green 144A. Under side: Near RHS Yellow-Green 144C.

Stipule:
*Arrangement*.—Opposite, occurring in pairs.
*Shape*.—Oblong.
*Average length*.—Approximately 2 cm.
*Average width*.—Approximately 1.3 cm.
*Apex*.—Rounded.
*Base*.—Truncate.
*Margin*.—Entire.
*Texture of top surface*.—Glabrous.
*Texture of lower surface*.—Glabrous.
*Color*.—Young foliage: Upper side: Near RHS Green 137A. Under side: Near RHS Green 138B.

FLOWER

Flower:
Bloom period: Flowering begins around the end of May, depending up temperature, in Washington, Ga. and persist for 2 to 3 weeks.

Flowers:
*Type and habit*.—Cup-shaped flowers occurring singly.
*Length*.—About 5 cm.
*Diameter*.—About 3.5 cm.

Bud:
*Shape*.—Oblong.
*Length*.—About 3.5 cm.
*Diameter*.—About 1.5 cm.
*Color*.—RHS Yellow-Green N144A.

Petals:
*Quantity*.—6.
*Length*.—5 cm.
*Width*.—2 cm.
*Apex*.—Acute or notched.
*Base*.—Rounded.
*Shape*.—Broad deltate.
*Margin*.—Entire.
*Texture*.—Glabrous, fleshy both surfaces.
*Color*.—Outer surface at opening: RHS Yellow-Green 154C. Triangular basal blotch near Yellow-Orange 22A. Inner surface at opening: RHS Yellow-Green 154C. Faint triangular basal blotch near Yellow-Orange 22C. Outer surface, mature: RHS Yellow 2C. Triangular basal blotch near Orange 26A. Inner surface, mature: RHS Yellow 2C. Triangular basal blotch near Orange 26B.

Peduncle:
*Length*.—4 to 5 cm.
*Diameter*.—4 mm.
*Color*.—RHS Yellow-Green 144C.
*Texture*.—Glabrous.
*Aspect*.—Upright.
*Strength*.—Very strong.

Calyx: Dehisces early.
*Length*.—About 2.5 cm.
*Width*.—1.5 cm.
*Color*.—RHS Yellow-Green 144C.

Sepals:
*Quantity*.—3.
*Length*.—2.5 cm.
*Diameter*.—9 mm.
*Color*.—RHS Yellow-Green 144C.
*Texture*.—Smooth, glabrous.
*Shape*.—Narrow deltate.
*Apex*.—Acute.
*Base*.—Truncate.
*Margin*.—Entire.

REPRODUCTIVE ORGANS

Stamens:
*Number*.—Average around 50 to 60.

Anthers:
*Shape*.—Imbricate.
*Length*.—5 mm.
*Width*.—2 mm.
*Color*.—RHS Yellow 7A.
*Pollen*.—Quantity: Scant. Color: RHS Yellow 9A.

Pistil:
*Number*.—Average 60 to 70 imbricate on central receptacle.
*Length*.—3 mm.
*Diameter*.—1 mm.
*Style*.—Length: 2 mm. Width: 1 mm. Color: RHS Yellow 7C.
*Stigma*.—Shape: Globular. Length: 1 mm. Width: 1 mm. Color: RHS Yellow 7A.
*Receptacle*.—Shape: Conical. Length: About 3.5 cm. Width: Base about 1.8 cm, apex about 8 mm. Color: RHS Yellow 4A.

OTHER CHARACTERISTICS

Disease/pest resistance: The breeder has observed no problems to date with powdery mildew, verticillium wilt, canker nor aphids.
Drought tolerance: No tolerance for drought observed.
Temperature tolerance: USDA Zones 4 through 9.
Fruits/nuts: Cone-like aggregate formed of samaras. This structure is on average 5 cm to 8 cm long and 1.5 cm in diameter. Colored near Grey-Brown N199D and 199A and 199B.

What is claimed is:

1. A new and distinct cultivar of *Liriodendron tulipifera* tree named 'LTMTF' as herein illustrated and described.

* * * * *